US008345513B2

(12) United States Patent  (10) Patent No.: US 8,345,513 B2
Huang                    (45) Date of Patent:     Jan. 1, 2013

(54) STACKED TRANSDUCING DEVICES

(75) Inventor: Yongli Huang, San Jose, CA (US)

(73) Assignee: Kolo Technologies, Inc., San Jose, CA (US)

( * ) Notice: Subject to any disclaimer, the term of this patent is extended or adjusted under 35 U.S.C. 154(b) by 68 days.

(21) Appl. No.: 12/745,749

(22) PCT Filed: Dec. 3, 2008

(86) PCT No.: PCT/US2008/085441
§ 371 (c)(1),
(2), (4) Date: Jun. 2, 2010

(87) PCT Pub. No.: WO2009/073748
PCT Pub. Date: Jun. 11, 2009

(65) Prior Publication Data
US 2010/0246332 A1    Sep. 30, 2010

Related U.S. Application Data

(60) Provisional application No. 60/992,020, filed on Dec. 3, 2007.

(51) Int. Cl.
*H04R 19/00* (2006.01)
(52) U.S. Cl. .................................................. 367/181
(58) Field of Classification Search .................... 367/181
See application file for complete search history.

(56) References Cited

U.S. PATENT DOCUMENTS

| | | | |
|---|---|---|---|
| 4,413,520 A * | 11/1983 | Murakami et al. | 73/609 |
| 4,603,589 A * | 8/1986 | Machida | 73/861.28 |
| 5,870,351 A | 2/1999 | Ladabaum et al. | |
| 5,872,536 A | 2/1999 | Lyons et al. | |
| 5,906,580 A | 5/1999 | Kline-Schoder et al. | |
| 5,957,851 A | 9/1999 | Hossack | |
| 6,493,288 B2 | 12/2002 | Khuri-Yakub et al. | |
| 6,558,330 B1 | 5/2003 | Ayter et al. | |
| 6,558,331 B1 * | 5/2003 | Davidsen et al. | 600/459 |
| 6,709,392 B1 | 3/2004 | Salgo et al. | |
| 6,776,763 B2 | 8/2004 | Nix et al. | |
| 6,854,338 B2 | 2/2005 | Khuri-Yakub et al. | |
| 6,945,115 B1 | 9/2005 | Wang | |
| 6,958,255 B2 | 10/2005 | Khuri-Yakub et al. | |
| 7,212,787 B2 | 5/2007 | Wu et al. | |
| 7,213,468 B2 * | 5/2007 | Fujimoto | 73/861.27 |

(Continued)

FOREIGN PATENT DOCUMENTS

WO    WO2006/123299    11/2006

(Continued)

OTHER PUBLICATIONS

Savoia, A.; Caliano, G.; Caronti, A.; Carotenuto, R.; Gatta, P.; Longo, C.; Pappalardo, M.; , "P2P-1 Multilayer cMUT Structure for Improved Sensitivity and Bandwidth," Ultrasonics Symposium, 2006. IEEE , vol., No., pp. 1939-1942, Oct. 2-6, 2006.*

(Continued)

*Primary Examiner* — Isam Alsomiri
*Assistant Examiner* — James Hulka
(74) *Attorney, Agent, or Firm* — Lee & Hayes, PLLC

(57) ABSTRACT

Implementations include a capacitive micromachined ultrasonic transducer (CMUT) having an additional transducing device overlaid in a vertically stacked relationship. In some implementations the additional transducing device is a second CMUT configured to operate at a different frequency from the first CMUT.

23 Claims, 13 Drawing Sheets

U.S. PATENT DOCUMENTS

| | | | |
|---|---|---|---|
| 7,305,883 B2 | 12/2007 | Khuri-Yakub et al. | |
| 7,408,283 B2 | 8/2008 | Smith et al. | |
| 7,880,565 B2 * | 2/2011 | Huang | 333/186 |
| 8,018,301 B2 * | 9/2011 | Huang | 333/186 |
| 2003/0236443 A1 * | 12/2003 | Cespedes et al. | 600/29 |
| 2004/0085858 A1 * | 5/2004 | Khuri-Yakub et al. | 367/181 |
| 2004/0229830 A1 * | 11/2004 | Tachibana et al. | 514/44 |
| 2005/0004466 A1 * | 1/2005 | Hynynen et al. | 600/449 |
| 2005/0015009 A1 * | 1/2005 | Mourad et al. | 600/438 |
| 2005/0137812 A1 * | 6/2005 | Schaffer et al. | 702/60 |
| 2005/0177045 A1 | 8/2005 | Degertekin et al. | |
| 2005/0288873 A1 * | 12/2005 | Urdaneta et al. | 702/45 |
| 2006/0004289 A1 * | 1/2006 | Tian et al. | 600/459 |
| 2006/0084875 A1 | 4/2006 | Knight | |
| 2006/0229659 A1 | 10/2006 | Gifford et al. | |
| 2007/0013269 A1 | 1/2007 | Huang | |
| 2007/0066902 A1 | 3/2007 | Wilser et al. | |
| 2007/0093702 A1 | 4/2007 | Yu et al. | |
| 2010/0013574 A1 * | 1/2010 | Huang | 333/186 |
| 2010/0160786 A1 | 6/2010 | Nordgren et al. | |
| 2011/0136284 A1 * | 6/2011 | Huang | 438/52 |

FOREIGN PATENT DOCUMENTS

| | | |
|---|---|---|
| WO | WO2006/123300 | 11/2006 |
| WO | WO2006/123301 | 11/2006 |

OTHER PUBLICATIONS

Chinese Office Action mailed Nov. 30, 2011 for Chinese patent application No. 200880117507.8, a counterpart foreign application of U.S. Appl. No. 12/745,758, 18 pages.

Non-Final Office Action for U.S. Appl. No. 12/326,769, mailed on Jun. 22, 2011, Yongli Huang, "Telemetric Sensing Using Micromachined Ultrasonic Transducer", 7 pages.

Chinese Office Action mailed Jan. 18, 2012 for Chinese patent application No. 200880117482.1, a counterpart foreign application of U.S. Appl. No. 60/992,020, 14 pages.

Office Action for U.S. Appl. No. 12/326,769, mailed on Dec. 9, 2011, Huang, "Telemetric Sensing Using Micromachined Ultrasonic Transducer", 8 pages.

Office action for U.S. Appl. No. 12/745,754, mailed on Jul. 5, 2012, Huang, "CMUT Packaging for Ultrasound System", 10 pages.

Office action for U.S. Appl. No. 12/745,754, mailed on Jan. 9, 2012, Huang, "CMUT Packaging for Ultrasound System", 10 pages.

Chinese Office Action mailed Jul. 25, 2012 for Chinese patent application No. 200880117507.8, a counterpart foreign application of U.S. Appl. No. 12/745,758, 7 pages.

Chinese Office Action mailed Aug. 24, 2012 for Chinese patent application No. 200880117483.6, a counterpart foreign application of U.S. Appl. No. 12/745,758, 29 pages.

* cited by examiner

STACKED TRANSDUCING DEVICES

CROSS-REFERENCE TO RELATED APPLICATION

This application claims the benefit of U.S. Provisional Patent Application No. 60/992,020, filed Dec. 3, 2007, the entire disclosure of which is incorporated herein by reference.

BACKGROUND

Various types of ultrasonic transducers have been developed for transmitting and receiving ultrasound waves. These ultrasonic transducers are commonly used in many applications including medical diagnostics and therapy, sonar and underwater imaging, biochemical imaging, non-destructive evaluation of materials, communication, proximity sensing, gas flow measuring, in-situ process monitoring, acoustic microscopy, and a variety of other uses. Ultrasonic transducers may be produced and/or used as single, discrete transducers. Further, ultrasonic transducer arrays that contain multiple transducers have also been developed. For example, two-dimensional arrays of ultrasound transducers can be used for 3-D imaging and other applications.

One type of ultrasonic transducer that has been developed is the micromachined ultrasonic transducer (MUT). Compared to the widely used piezoelectric (PZT) ultrasound transducer, the MUT has advantages in fabrication methods, operation bandwidth and operating temperatures. For example, PZT transducers are typically produced by making arrays of transducers, dicing the arrays, and connecting individual piezoelectric elements. This manufacturing technique can be fraught with difficulty and expense, and the PZT transducers themselves may have a large impedance mismatch problem. On the other hand, MUTs can be manufactured using more efficient semiconductor micromachining techniques, and MUTs demonstrate a comparable dynamic performance to PZT transducers. For these reasons, the MUT is becoming an attractive alternative to the piezoelectric ultrasound transducer.

One type of MUT that is widely used is the CMUT (capacitive micromachined ultrasonic transducer), which uses electrostatic attraction between electrodes. For example, a CMUT having embedded springs and surface plates (ESCMUT) has been recently developed to improve device performance. The basic structure of an ESCMUT is a surface plate or multiple surface plates that are supported by embedded springs in a micromachined structure. However, while the CMUTs developed thus far demonstrate better performance than PZT transducers in most device parameters, CMUTs may still be improved to enable CMUTs to outperform PZT transducers in every application field.

BRIEF DESCRIPTION OF THE DRAWINGS

The accompanying drawing figures, in conjunction with the description, serve to illustrate and explain the principles of the best mode presently contemplated. In the figures, the left-most digit of a reference number identifies the figure in which the reference number first appears. In the drawings, like numerals describe substantially similar features and components throughout the several views.

DETAILED DESCRIPTION

Figure 1:
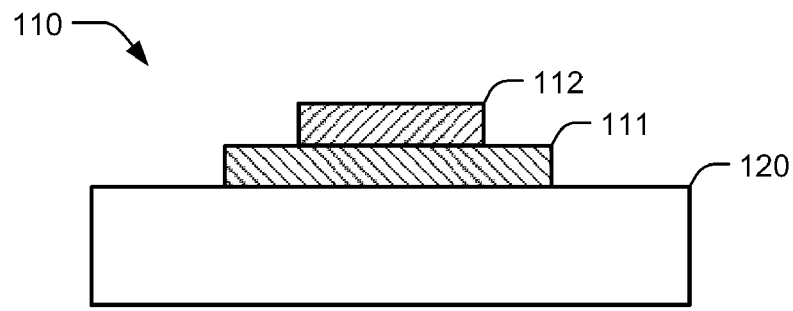
FIG. 1 illustrates an exemplary implementation of a component having a transducing device stacked on a CMUT.

In the following detailed description, reference is made to the accompanying drawings which form a part of the disclosure, and in which are shown by way of illustration, and not of limitation, exemplary implementations. Further, it should be noted that while the description provides various exemplary implementations, as described below and as illustrated in the drawings, this disclosure is not limited to the implementations described and illustrated herein, but can extend to other implementations, as would be known or as would become known to those skilled in the art. Reference in the specification to "one implementation", "this implementation", "some implementations" or "these implementations" means that a particular feature, structure, or characteristic described in connection with the implementations is included in at least one implementation, and the appearances of these phrases in various places in the specification are not necessarily all referring to the same implementation. Additionally, in the description, numerous specific details are set forth in order to provide a thorough disclosure. However, it will be apparent to one of ordinary skill in the art that these specific details may not all be needed in all implementations. In other circumstances, well-known structures, materials, circuits, processes and interfaces have not been described in detail, and/or may be illustrated in block diagram form, so as to not unnecessarily obscure the disclosure.

Implementations disclosed herein relate to micromachined ultrasonic transducers (CMUTs). Some implementations are directed to a CMUT arrangement with stacked features and provide methods of implementation for various applications. Some implementations include a second functional structure, which will be referred to as a transducing device, built upon a CMUT. As used herein, a transducing device may be any transducer, sensor or other device that is able to convert or exchange energy. In some implementations, the stacked feature comprises a second CMUT structure built upon a first CMUT structure, so that two CMUT structures are stacked, one on top of the other. Some implementations also include methods of operating of two stacked CMUTs.

Furthermore, some implementations are based on a CMUT with embedded springs (ESCMUT). In some implementations, the second structure can be built on a surface plate of the CMUT. The second structures may be transducing devices that include interface circuits, sensors, or transducers, e.g., pressure sensors, temperature sensors, flow sensors, a CMUT structure, or the like. Moreover, in some implementations, if the surface plate of the first CMUT is designed to be relatively rigid, the top plate of the transducer may serve as a platform for such additional fabrication of a second structure. When incorporated using a proper design, the CMUT and the additional features or structures built on the top of the CMUT may be operated independently.

In some implementations, two CMUT structures can be built contiguously, one on the other, based on an ESCMUT design. For example, the first CMUT structure may be formed between an electrode related to a spring layer and an electrode related to a substrate. The second structure may then be formed between the electrode related to the spring layer and an electrode related to the surface plate. Furthermore, in some implementations, the surface plate of the CMUT can be patterned to a certain shape to improve CMUT performance, as well as to minimize the interference between the operation of two CMUT structures.

In some implementations disclosed herein, the focus is on a transducer component with two stacked CMUT structures. The stacked CMUT structures may be used in different combinations to achieve desired functions and performance for selected applications, such as separate transmission and reception functions, double transmission, double reception, or independently operated CMUTs, as is discussed further below. The approach set forth herein not only greatly improves the CMUT design flexibility to adapt to an ultrasound system, but is also able to dramatically improve the transducer performance. In some implementations, the locations of two stacked transducer structures are defined by lithography, thus enabling the accurate registration of two transducers, one constructed on top of the other. The CMUT structures in the stacked CMUT configurations disclosed herein can be designed to be any configuration, e.g., a single element transducer, a 1-D array, 1.5-D array, 1.75-D array, 2-D array or annular array etc. Also two stacked CMUT structures may have the same or different configurations.

In some implementations, the stacked structures preserve the transducer area that is important for transrectal, intracavitary and intravascular applications. One application for implementation of the transducers with stacked CMUT structure is HIFU (high intensity focused ultrasound), which may be used for tissue ablation, treatment of prostate cancer, and the like. Another application for implementations disclosed herein is IVUS (intravascular coronary ultrasound) which is used for intravascular imaging.

FIG. 1 illustrates an implementation of a component 110 that includes CMUT 111 having a transducing device 112 located thereon in a stacked or overlaid configuration. CMUT 111 may be located on a substrate 120, which may be a separate support surface (e.g., part of probe), other suitable support, or just part of CMUT 111 itself, depending on the intended application of component 110. In various implementations, transducing device 112 can be one or more circuits, sensors, transducers or any combination thereof, depending on an intended application of component 110. For example, transducing device 112 may be a transducer interface circuit, a pressure sensor, a temperature sensor, a flow sensor, or the like.

Implementations disclosed herein include a multiple transducer design in which a second CMUT structure is located on a first CMUT structure, such that the second CMUT is located on top of the first CMUT, or vice versa. In implementations of component 110 having two stacked or overlaid CMUT structures, transducing device 112 of component 110 may comprise the second CMUT and CMUT 111 may be the first CMUT, or vice versa, so that component 110 forms a stacked transducer made up of stacked CMUT structures. The stacked CMUT structures may be used in different combinations to achieve a desired function and performance for a selected application. Examples of various applications for a stacked CMUT structure include enabling separate transmission and reception, double transmission, double reception, or independently operated CMUTs. For instance, the two CMUT structures may have the same or different characteristics. This approach not only greatly improves the CMUT design flexibility to adapt to an ultrasound system, but may also dramatically improve the transducer performance. The stacked structures preserve the transducer area that is important for transrectal, intracavitary and intravascular applications, such as for HIFU applications, IVUS applications, or the like.

The CMUTs in the stacked transducer component can be designed to be any configuration, e.g., a single element transducer, 1-D array, 1.5-D array, 1.75-D array, 2-D array, an annular array, etc. Also, the two stacked CMUT structures may be CMUTs having the same configuration or different configurations. For example, the two stacked CMUT structures may be designed to operate in the same center frequency or different center frequencies.

The basic structure of a CMUT acts as a variable capacitor which has at least one electrode that is moveable to exchange energy between an electrical field and an acoustic field. Further, when multiple CMUTs are configured as an array structure, then each CMUT element in the array can be symbolically represented as a variable capacitor and, thus, the CMUT array can be symbolically represented by an array of variable capacitors.

The stacked CMUT structures, 111 and 112 in the component 110 illustrated in FIG. 1 may be wired and configured in various ways to realize certain desired function or performance. Examples of several various connection schemes are illustrated with references to FIGS. 2-5, although other possibilities will be apparent to those of skill in the art in view of the disclosure herein. In the figures, an addressable CMUT element in a CMUT structure may be symbolically represented as a capacitor (C). Further, in implementations in which a CMUT structure is an array, only one element may be illustrated in the figures.

Figure 2:
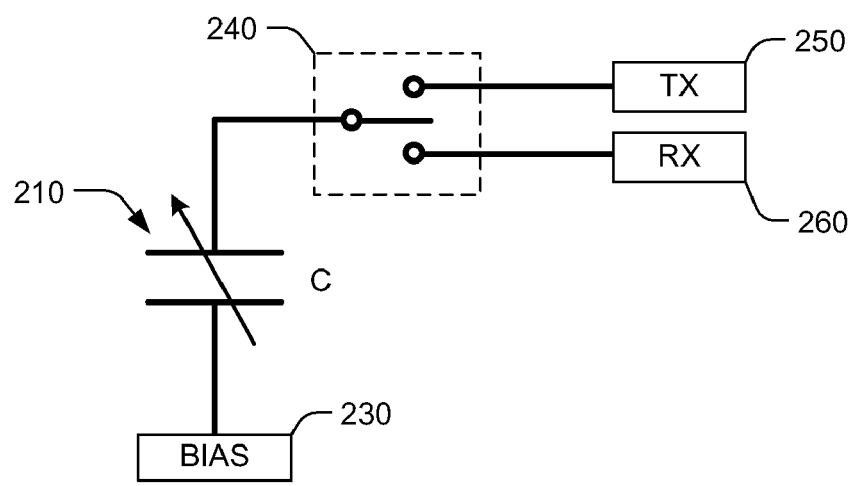
FIG. 2 illustrates an exemplary implementation of a system including a CMUT connection arrangement.

FIG. 2 illustrates an exemplary system 200 implementing a connection scheme in which a single CMUT 210 (represented schematically as a variable capacitor C) is used alternately for both transmission and reception of acoustic energy. CMUT 210 is connected on one side to a bias circuit or desired bias voltage source 230. CMUT 210 is connected on the other side to a switch 240. Switch 240 may connect CMUT 210 to either a transmission interface circuit 250 or a reception interface circuit 260. For instance, when switch 240 connects CMUT 210 to transmission interface circuit 250, a voltage may be applied to cause CMUT 210 to transmit acoustic energy. On the other hand, when switch 240 connects CMUT 210 to reception interface circuit 260, signals representing acoustic energy detected by CMUT 210 may be passed to reception interface circuit 260. Further, it should be noted that switch 240 may be an actual switch circuit, may be a protection circuit for a detection circuit during transmission, or other device or circuit accomplishing a similar function.

Figure 3:
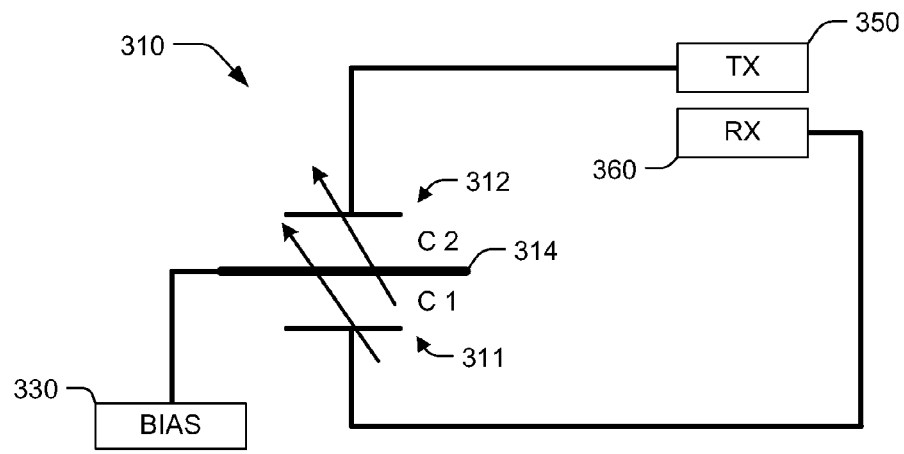
FIG. 3 illustrates an exemplary implementation of a connection arrangement for stacked CMUTs.

Stacked CMUT structures in accordance with implementations disclosed herein enable various alternative connection arrangements. FIG. 3 illustrates a system 300 implementing a first exemplary connection arrangement in which a component 310 includes two stacked CMUT structures made up of a first CMUT (C1) 311 and a second CMUT (C2) 312, one of which is used for transmission and the other of which is used for reception. The stacked CMUTS are symbolically represented as variable capacitors representing the CMUT structures, an may be configured in the same manner as CMUT structures 111 and 112 of FIG. 1, or in accordance with other implementations disclosed herein above and below. CMUT 311 and 312 may be connected to a bias or a desired voltage source 330 through a middle electrode 314, which may be a common middle electrode in some implementations, or two separate middle electrodes in other implementations. In the illustrated implementation, second CMUT 312 is dedicated to transmission through transmission interface circuit 350 and first CMUT 311 is dedicated to reception through reception interface circuit 360.

The arrangement illustrated in FIG. 3 may have a number of advantages over the implementation of FIG. 2. For example, a switch circuit is not required to protect the reception circuit 360, which may have a preamplifier or other sensitive components. An electrical signal from transmission circuit 350 is shielded by the common middle electrode 314 connected to the bias or a desired voltage source 330, so that cross talking between transmission and reception is minimized. As a result, the front-end reception circuit 360 can be optimized without being concerned about issues such as saturation from the coupling of a transmission signal from transmission circuit 350. Furthermore, since the transmission and reception operation use different CMUT structures, there is no need to make a design trade-off between transmission and reception performances, i.e., first CMUT 311 can be optimized for reception performance and second CMUT 312 can be optimized for transmission performance.

Figure 4:
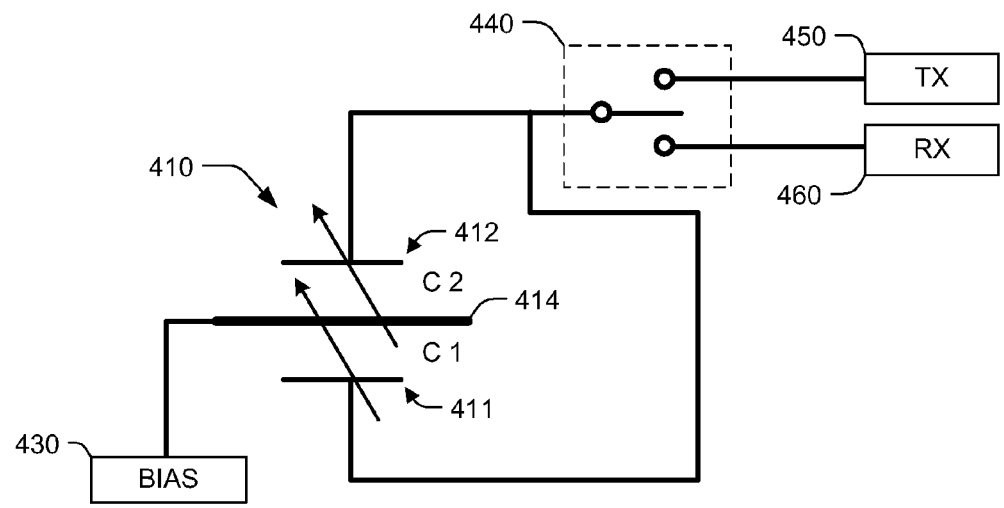
FIG. 4 illustrates another exemplary implementation of a connection arrangement for stacked CMUTs.

In addition, depending on the desired application, the CMUT structures enabled by implementations disclosed herein may be configured in a variety of other arrangements. FIG. 4 illustrates an exemplary system 400 including a connection arrangement in which a component 410 includes two CMUT structures connected in parallel. A first CMUT (C1) 411 and a second CMUT (C2) 412 are arranged in a stacked configuration as discussed above with respect to FIG. 1. Stacked CMUT structures 411, 412 are connected to a bias or a desired voltage source 430 through a middle electrode 414, which may be a common electrode of CMUTs 411, 412 in some implementations, or which may be two separate electrodes in other implementations.

In the illustrated arrangement, both CMUTs 411, 412 are configured to be selectively dedicated either to transmission or reception through activation of a switch 440, by setting switch 440 to either connection with a transmission circuit 450 or a reception circuit 460, respectively. Further, it should be noted that switch 440 may be an actual switch circuit, may be a protection circuit for a reception circuit during transmission, or other device or circuit accomplishing a similar function. Since both CMUT structures 411, 412 in component 410 contribute to the transmission and reception performances of the transducer, the performance of component 410 can be the combination of the performance the two CMUT structures 411, 412, which greatly improves component performance and design flexibility.

For example, when the two CMUT structures 411, 412 are configured to have similar frequency response, then the performance of both transmission and reception of the transducer may be sum of two CMUT structures. On the other hand, when the two CMUT structures 411, 412 are configured to have different frequency responses which compensate for each other, then the bandwidth of component 410 may cover the bandwidths of both CMUT structures so as to achieve a very wide bandwidth that a conventional single transducer would not be able to achieve. For example, if the frequency responses of the two CMUT structures 411, 412 are separated, then the stacked CMUT structures 411, 412 may be operated efficiently in two separate frequency ranges as two independent CMUT transducers.

Figure 5:
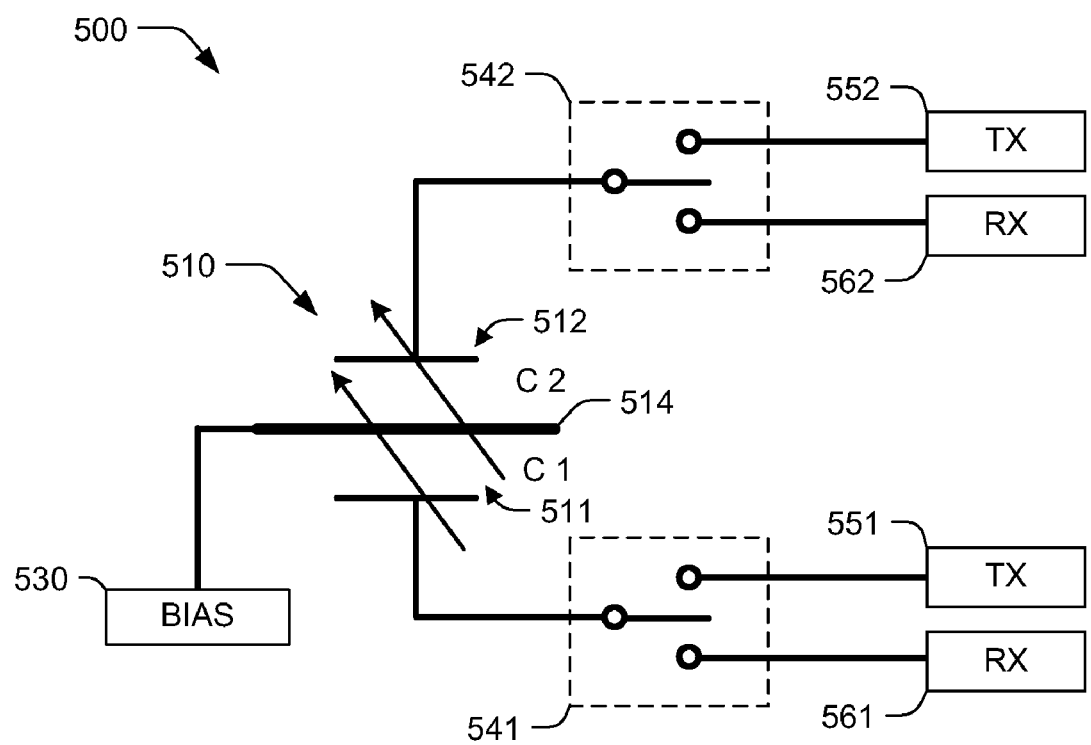
FIG. 5 illustrates another exemplary implementation of a connection arrangement for stacked CMUTs.

FIG. 5 illustrates another exemplary system 500 including a connection arrangement for a component 510 including a first CMUT structure (C1) 511 in a stacked or overlaid configuration with a second CMUT structure (C2) 512. CMUTs 511, 512 may be connected separately as independently addressed CMUTs, and are connected to a bias or a desired voltage source 530 through a middle electrode, which may be a common electrode of CMUTs 511, 512 in some implementations, or which may be two separate electrodes in other implementations. A first switch 541 is selectively actuatable to connect first CMUT 511 to one of a first transmission circuit 551 or a first reception circuit 561. Similarly, a second switch 542 is selectively actuatable to connect second CMUT 512 to one of a second transmission circuit 552 or a second reception circuit 562. First transmission circuit 551 and second transmission circuit 552 may be the same circuit in some implementations, or separate circuits in other implementations. Similarly, first reception circuit 561 and second reception circuit 562 may be the same circuit in some implementations, or separate circuits in other implementations. Further, as with the implementations discussed above, switches 541, 542 may be an actual switch circuits, may be protection circuits for a reception circuit during transmission, or other device or circuit accomplishing a similar function.

The connection scheme illustrated in FIG. 5 has a great deal of flexibility to achieve desired transducer performance and may be adapted for a variety of different applications, but has higher connection complexity and requires more hardware than the implementations illustrated in FIGS. 2-4. Functionally, the connection arrangement of FIG. 5 can be configured to perform all possible functions of connection schemes in the previous example implementations of FIGS. 2-4. Thus, in some configurations of the implementation of FIG. 5, first CMUT 511 may be configured in a transmission mode, while second CMUT 512 may be configured in a reception mode, or vice versa. Alternatively, both CMUT 511 and CMUT 512 may be configured in the same mode at the same time. Further, CMUTs 511 and 512 may have similar or different transmission and receptions capabilities.

Implementations of components having stacked CMUT structures as disclosed herein may provide significant benefits in some applications (e.g., medical applications such as HIFU, intravascular or other intracavitary applications) which allow limited operating space, or in applications that require a level of performance (e.g., working in multiple frequency bands or extremely wide bandwidths) that a conventional transducer cannot achieve. Further, implementations of the components disclosed herein having stacked CMUT structures can be configured to function properly, even when two overlaid CMUT structures operate relative independently of each other.

Figure 6:
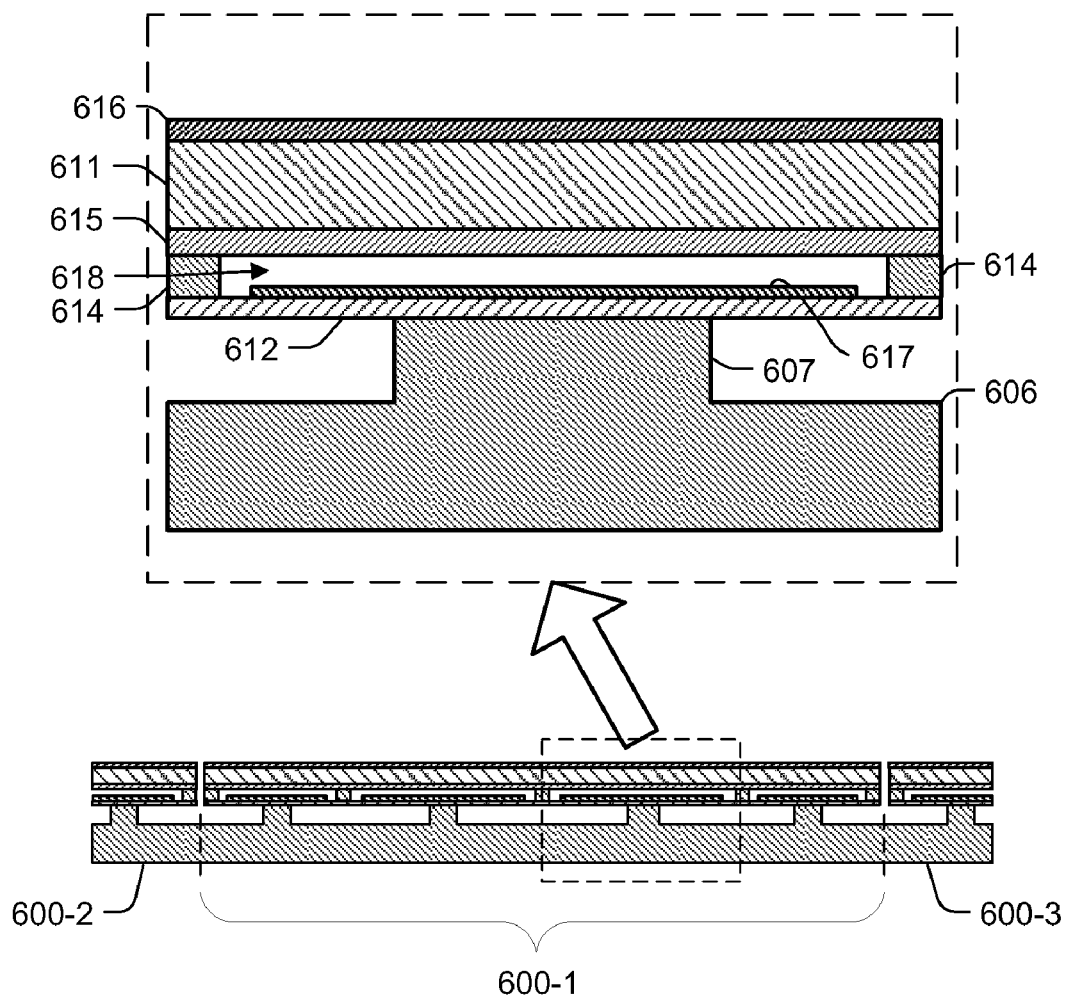
FIG. 6 illustrates a cross-sectional view of an exemplary implementation of a component.

Some implementations disclosed herein incorporate a CMUT design having one or more embedded springs (ESCMUT). FIG. 6 is a cross-sectional view of an ESCMUT structure illustrating a complete CMUT element 600-1 and parts of neighboring CMUT elements 600-2 and 600-3, one on each side of CMUT element 600-1. The enlarged view of a section (unit) of the CMUT element 600-1 is illustrated within a rectangle of dashed lines above the complete CMUT element. The CMUT 600-1 is built on a substrate wafer 606 having a raised support 607. A spring member 612 contacts raised support 607 and includes a first electrode 617 formed thereon. Connector supports 614 maintain a plate second electrode 611 in a spaced relationship from electrode 617. Plate 611, which serves as the second electrode, may be relatively rigid, and optionally includes a first insulation layer 615 and a second insulation layer 616. In the ESCMUT implementation illustrated in FIG. 6, the top plate is separated from spring member 612 and first electrode 617 by the connector supports 614 to define a gap or cavity 618 there between. Plate 611 may include the second electrode formed integrally, such as by doping, or the second electrode may be a separate layer deposited on plate 611. Further, first electrode 617 may be formed on or as part of spring member 612, or alternatively, may be formed on or as part of substrate 606 below spring member 612.

As an explanation of how ESCMUT 600-1 functions, in transmission mode, for example, a voltage is applied between first electrode 617 and second electrode 611, causing an electrostatic attraction. Due to the electrostatic attraction, first electrode 617 and second electrode 611 move toward each other, thereby flexing spring member 612. When the voltage is removed, the restorative spring force of spring member 612 causes first electrode 617 and second electrode 611 to move away from each other back toward an initial position. Similarly, in a reception mode, acoustic energy impinges ESCMUT 600-1, causing the second electrode 611 to move relative to the first electrode 617, changing a capacitance between the first electrode 617 and second electrode 611, and the restorative force of spring member 612 urges a return toward the initial position.

Because the plate/second electrode 611 of a CMUT configured with an embedded spring member may be designed to be relatively rigid, the plate of the CMUT is able to serve as a platform for one or more additional functional devices, such as one or more additional transducers. The additional functional devices may be transducing devices including any integrated circuits, sensors or transducers which can be fabricated on plate 611 to achieve a desired function for a desired application. Further, by implementing proper design configurations as described herein, the CMUT and the additional functional devices on the top of the CMUT are able to be operated independently.

Figure 7:
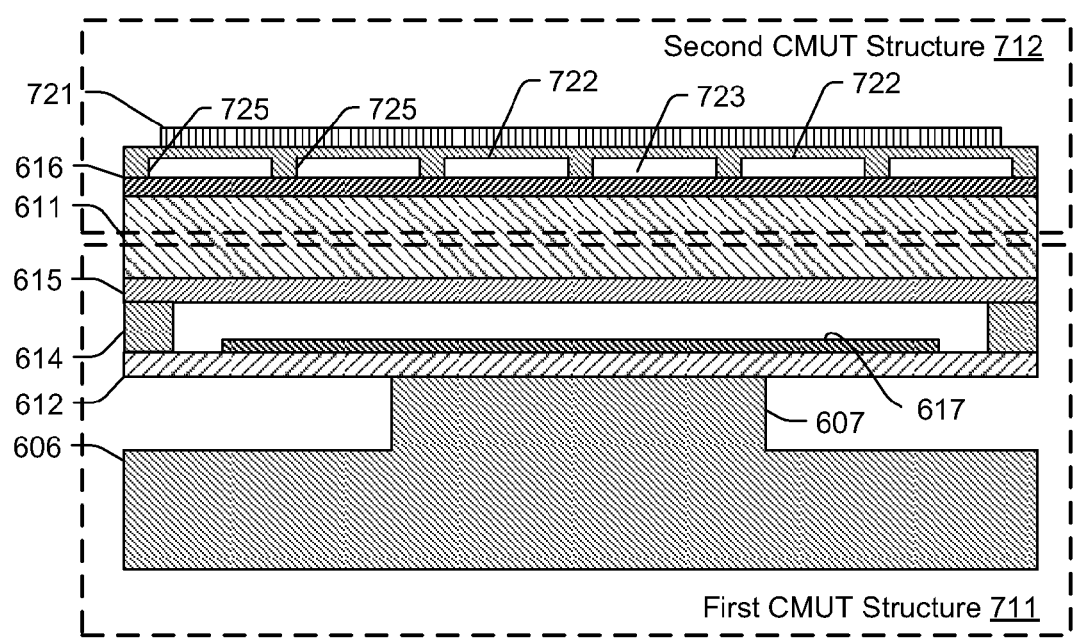
FIG. 7 illustrates a cross-sectional view of an exemplary implementation of a component including a first CMUT and a second CMUT.

In particular implementations of a CMUT with a stacked transducing device, an ESCMUT with embedded spring may comprise a first CMUT structure, which may correspond to the CMUT 111 of FIG. 1, and a second CMUT structure may correspond to the transducing device 112 of FIG. 1. FIG. 7 illustrates an exemplary component 700 having stacked CMUT structures in accordance with the ESCMUT configuration described above with reference to FIG. 6. In the illustrated implementation, regions for the two stacked CMUT structures are identified by dash-lined rectangles. A first region encompasses a first CMUT structure 711 and a second region encompasses a second CMUT structure 712. Thus, the first CMUT 711 and the second CMUT 712 are contiguous and overlaid one on top of the other in a direction of transmission and/or reception of acoustic energy. First CMUT structure 711 may be a transducer based on the ESCMUT 600 described above, so that plate 611 can serve as the base for second CMUT structure 712, and also can serve as one of the electrodes for second CMUT structure 712. Second CMUT structure 712 in the exemplary stacked CMUT component 700 illustrated in FIG. 7 is a transducer based on a flexible membrane CMUT design. However, in other implementations, second CMUT structure 712 may also be constructed as an ESCMUT 600 with embedded spring member. Plate 611 serves as a common electrode of the two CMUT structures 711, 712, and may serve as the ground or a bias electrode, as discussed above with reference to FIGS. 3-5. Therefore plate 611 is able to shield the electrical coupling between the two CMUT transducers 711, 712 during device operation.

In the second CMUT structure 712 in the exemplary stacked CMUT component 700, plate 611 of the first CMUT structure 711 also serves as the substrate of the second CMUT structure 712. Second CMUT structure 712 also includes a third electrode 721 formed on a spring-like flexible element 722, such as a flexible membrane. Flexible element 722 is supported by flexible element supports 725 to provide and maintain a gap or cavity 723 between flexible element 722 and optional insulation layer 616. Thus, flexible element 722 enables third electrode 721 to move toward second electrode 611, while a restorative elastic or spring force of the flexible element 722 urges the flexible element 722 and third electrode 721 to return back toward an initial position (e.g., an at-rest or equilibrium position). Further, while flexible element 722 and third electrode 721 are illustrated as being separate in FIG. 7, it should be understood that third electrode and flexible element 722 may be one and the same, i.e., flexible element 722 may be conductive and also act as third electrode 721, or third electrode 721 may be embedded in flexible element 722, or the like. With proper design for operating frequency, bandwidth, and the like, first CMUT structure 711 and second CMUT structure 712 may operate independently of each other, especially when the two CMUTS 711, 712 operate in separate frequency ranges.

Figure 8A:
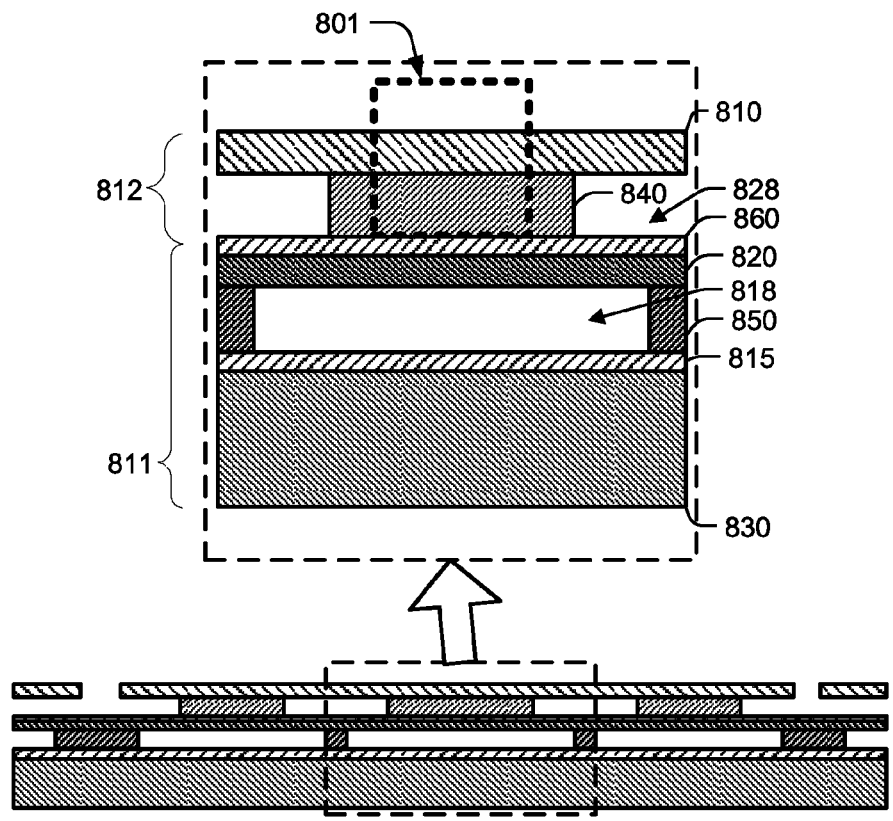
FIG. 8A illustrates a cross-sectional view of an exemplary implementation of a component including first CMUT and a second CMUT.

FIG. 8A illustrates another implementation in which two CMUT structures are constructed based on a modified configuration of a single ESCMUT. In FIG. 8A, a component 800a includes a first plate 810 that is configured to serve as a top electrode and a substrate 830 that is configured to serve as a bottom electrode. A common middle electrode 860 is included at a spring member 820, either as part of spring member 820, formed thereon, or the like. Substrate/bottom electrode 830 includes an optional insulation layer 815, and is supported in a spaced relationship from spring member 820 by spring anchors 850 which serve as first supports to create and maintain a first gap or cavity 818. Accordingly, spring member 820 and middle electrode 860 are able to flex toward bottom electrode 830, such as when component 800a is impinged by acoustic energy, or when an electrostatic charge is applied between bottom electrode 830 and middle electrode 860. When spring member 820 is flexed toward bottom electrode 830, a restorative spring force of spring member 820 urges spring member 820 and middle electrode back toward an at-rest position. Thus, in this implementation, a first CMUT structure 811 is formed between the middle electrode 860 related to the spring member 820 and the bottom electrode formed as the substrate 830. A second CMUT structure 812 is formed between the middle common electrode 860 and the top electrode formed as plate 810. Plate supports 840 serve as second supports to create and maintain a second gap or cavity 828 between plate/top electrode 810 and middle electrode 860, so that plate 810 is able to flex toward middle electrode 860, such as when plate 810 is impinged by acoustic energy, or when an electrostatic charge is applied between plate 810 and middle electrode 860. A restorative spring force of plate 810 urges plate 810 back to an initial position (e.g., an at-rest or equilibrium position) when plate 810 is flexed toward middle electrode 860, in the manner discussed above with respect to flexible element 722 of the implementation of FIG. 7. Thus, the first CMUT 811 and the second CMUT 812 are contiguous and stacked, one on top of the other, in a direction of transmission and/or reception of acoustic energy.

The flexibility of the plate 810 is always a relative property and is strongly dependent on an operation frequency of the CMUT. When the single ESCMUT (shown in FIG. 8A) is configured to perform as the two stacked CMUT structures by adding the second capacitive structure, the flexibility of the surface plate 810 can be designed according to the predetermined operating frequencies or methods. If two stacked CMUT structures are designed to operate at similar frequency, the plate 810 can be designed to be either flexible or rigid at the operation frequency. If two stacked CMUT structures are designed to operate at two different frequencies as disclosed in some implementations herein, the first CMUT structure 811 is usually designed to operate at first frequency, such as a low frequency, and so the surface plate 810 should be designed to be rigid at the first frequency so that the first CMUT structure 811 operates like a normal ESCMUT. The second CMUT structure 812 is usually designed to operate at second frequency, such as a high frequency, and so the surface plate 810 should be designed to be flexible at the second frequency so that the second CMUT structure 812 operates like a normal flexible membrane CMUT. If the difference between the first frequency and the second frequency is designed to be large enough, there is almost no interference between the operation of the two stacked CMUT structures 811, 812 even though they are contained in a single ESCMUT device. The interference between the two CMUT structures can be further minimized with the implementation of the design in FIG. 8B described below.

Figure 8B:
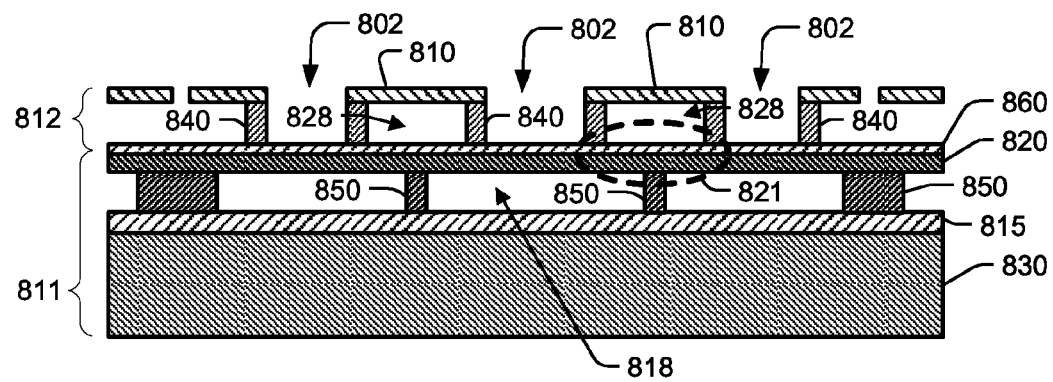
FIG. 8B illustrates a cross-sectional view of an exemplary implementation of a modified component of FIG. 8A.

Furthermore, in the implementation of component 800a illustrated in FIG. 8A, plate 810 of component 800 can be patterned to a certain predetermined shape to improve performance of second CMUT structure 812, as well as to further minimize the interference between operation of the first CMUT 811 and the second CMUT 812. One exemplary implementation is illustrated as component 800b in FIG. 8B. In FIG. 8B, a portion of plate 810 and plate support 840 is removed to create channels 802 by removing material from plate 810 and plate supports 840, such as indicated by bold dashed line 801 in FIG. 8A. In the implementation of FIG. 8B, the bottom CMUT structure 811 has a small equivalent mass and a large surface displacement. The top CMUT structure resides on a relatively inactive area 821 of the spring member 820 (i.e., over spring anchor 850) so that there is minimum interference between the two CMUT structures 811, 812. For example, because the patterned plate 810 is located primarily over one or more of the spring anchors 850, CMUT 812 is mostly operative over spring anchors 850, so that the flexing of plate 810 toward middle electrode 860 during operation of second CMUT 812 has minimal effect on the flexing of spring member 820 and middle electrode 860 toward first electrode 830 during operation of first CMUT 811.

Additional embodiments are directed to a pressure sensor or flow sensor as transducing device 112 stacked on a CMUT 111 of FIG. 1. For example, the basic structure of a micromachined pressure sensor is similar to a CMUT structure. Depending on the design and the functionality, the second CMUT structures disclosed herein may be configured and designed to serve as a pressure sensor or a flow sensor. For example, in some implementations, the pressure information or the flow information is extracted from an output signal of a CMUT structure by using a modulation method for determining pressure or flow information. Applying modulation signals to CMUTs is disclosed in PCT Application No PCT/US2007/065888, filed Apr. 3, 2007, to the same inventor as herein, the entire disclosure of which is incorporated herein by reference.

Figure 9:
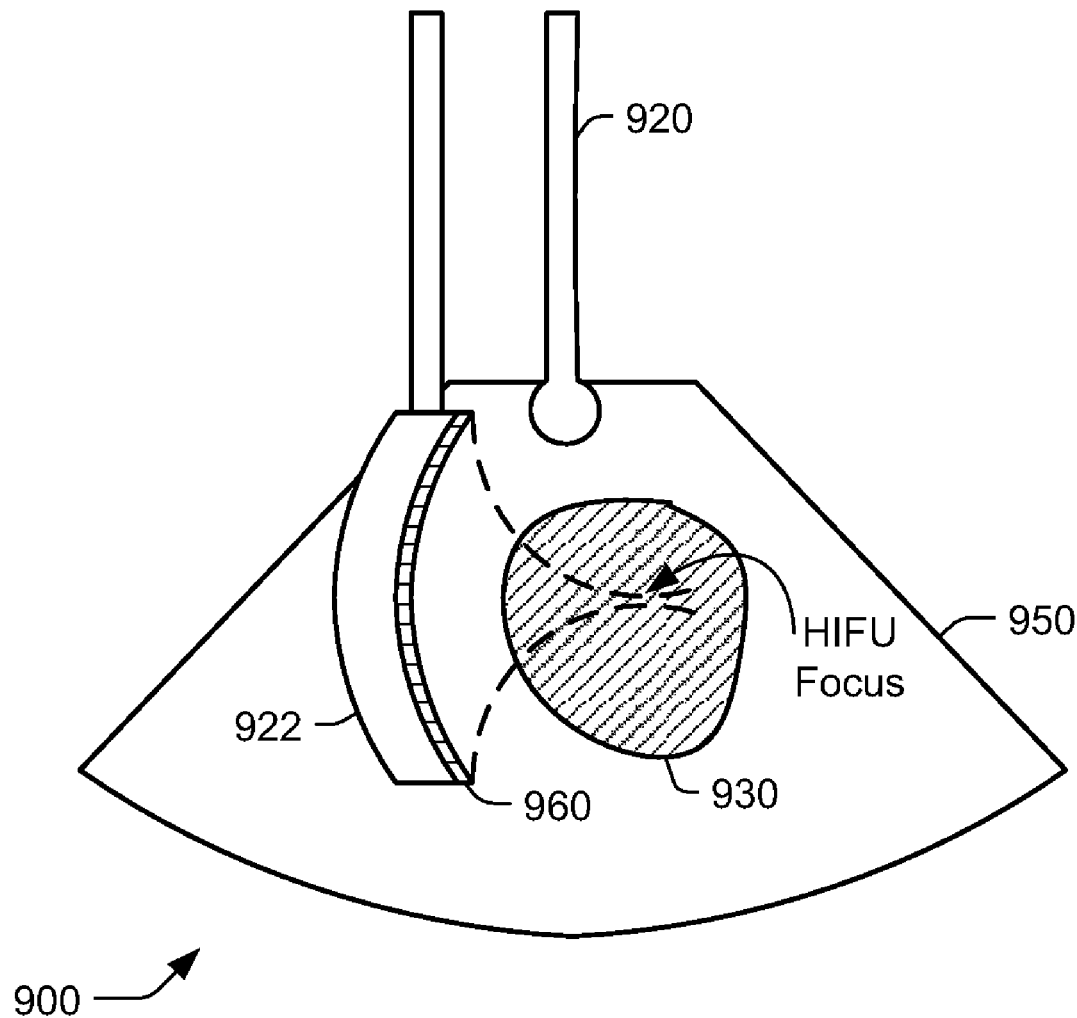
FIG. 9 illustrates an example of a system including separate ultrasound imaging and HIFU probes.

One exemplary application of implementations of components having stacked CMUT structures is for prostate cancer diagnosis and treatment using high intensity focused ultrasound (HIFU). Typically, the diagnosis, treatment and treatment assessment are carried out using different transducers or systems. For example, MRI (magnetic resonance imaging) and other imaging methods are usually used to perform imaging and treatment assessment in a HIFU procedure. Further, ultrasound imaging may be desired to be used to provide guidance during a HIFU procedure, such as during treatment of prostate cancer. However, conventional ultrasound imaging from the outside of the body cannot provide the high-quality images necessary for proper prostate cancer treatment and assessment. Therefore, as illustrated in a system 900 of FIG. 9, a transrectal ultrasound-imaging probe 920 may be used in conjunction with a HIFU probe 922 during a procedure to focus ultrasound energy on a portion of a prostate 930 for carrying out tissue ablation, or the like. Thus, a conventional HIFU system 900 requires at least two probes, e.g., both imaging probe 920 which provides a field of view 950 for locating the prostate, and a HIFU probe 922 that includes an ultrasonic transducer 960 for directing ultrasonic energy at a portion of the prostate 930. However, there are a few disadvantages to putting both the imaging probe 920 and the HIFU probe 922 into a patient's rectum during treatment due to the very limited space. In addition, errors may occur in the registration of the positions of the imaging probe 920 and the HIFU probe 922 because of the potential for relative movement between the two probes (e.g., rotation, bending, shifting, etc.).

Implementations disclosed herein enable a HIFU procedure to be performed using a single probe for both treatment and imaging/treatment assessment. Since one normal transducer or transducer array may not be sufficient to perform both imaging and treatment, implementations disclosed herein provide two transducers or transducer arrays located on a single probe. Implementations of the components disclosed above having overlaid CMUT structures make it possible to perform imaging, diagnosis, treatment, and real-time assessment of the treatment using a single probe. Implementations of probes disclosed herein include two independently operated CMUTs stacked vertically in relation to each other on a single probe. The two stacked CMUTs, one of which may be used for imaging and the other of which may be used for treatment, can be placed at the same location as a single transducer in conventional probes. Thus, implementations disclosed herein provide for compact transducer components that are more suitable for applications which have limited space, such as surgical applications. Furthermore, providing two stacked CMUT structures in a single component enables accurate registration of the treatment and assessment probes because there is no chance of relative movement between the two during use, which is a difficult task using conventional systems.

Figure 10A:
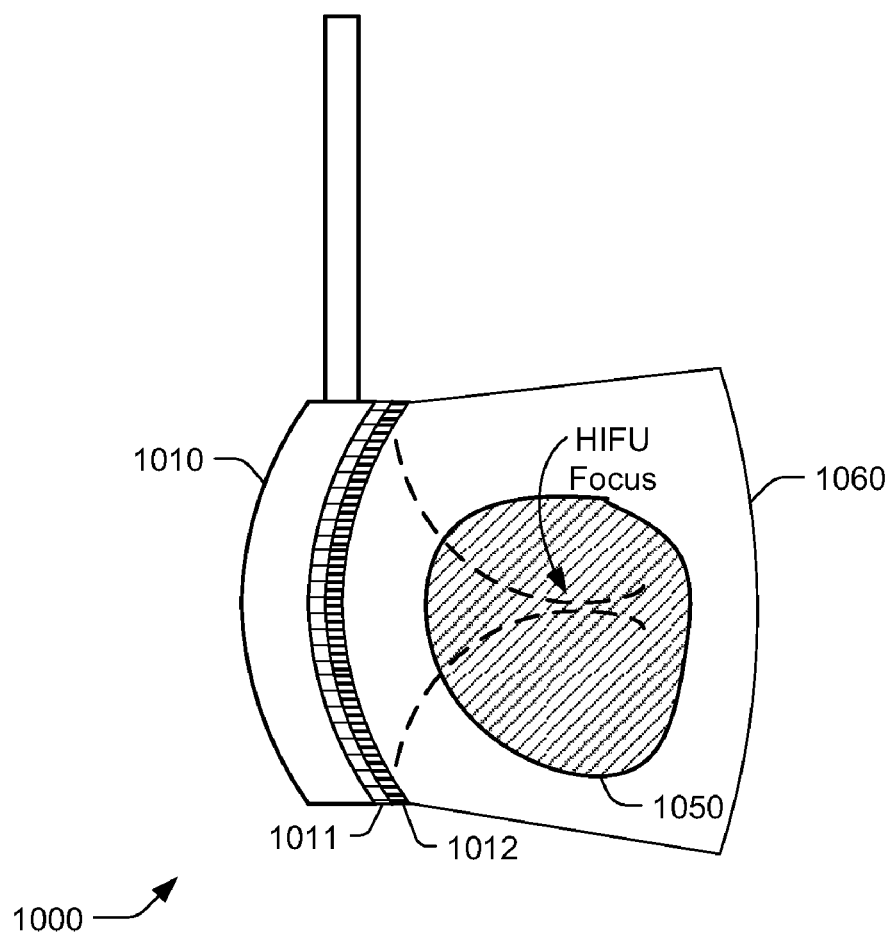
FIGS. 10A-10B illustrate an exemplary implementation of a system including a component having stacked CMUTs.
Figure 10B:
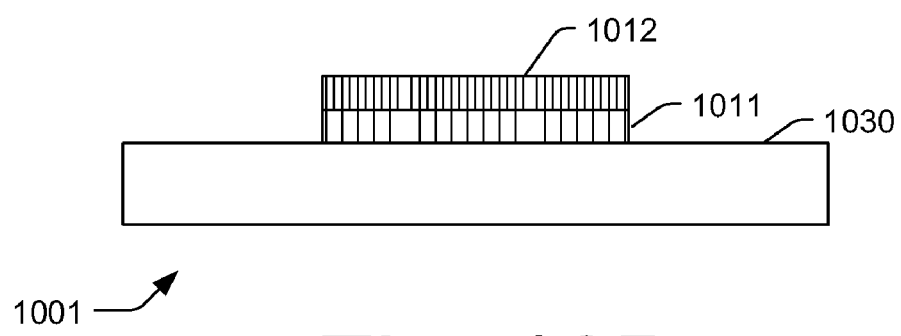

An exemplary implementation of a system 1000 including stacked CMUT structures is illustrated in FIGS. 10A-10B. FIG. 10A depicts a probe 1010 that comprises a first transducer 1011 and a second transducer 1012 vertically packaged on the single probe 1010, such that second transducer 1012 is stacked and overlaid on first transducer 1011. One example of possible use for probe 1010 is performing both treatment and imagining in a HIFU procedure. For example, one of transducers 1011, 1012 may be used for imaging operation for providing a field of view 1060 of a prostate 1050 and the other transducer 1011, 1012 may be used for HIFU operation to focus ultrasonic energy on a desired area of the prostate 1050.

FIG. 10B illustrates an exemplary configuration of a component 1001 that may be used on probe 1010 illustrated in FIG. 10A. Component 1001 includes first CMUT structure 1011 and second CMUT structure 1012 are vertically integrated on the same substrate 1030 in an overlaid relationship, such that second CMUT 1012 is located on top of first CMUT 1011 relative to a direction of transmission and/or reception. The CMUT structures 1011, 1012 of FIGS. 10A-10B may be designed to be any CMUT configuration, e.g., a single element transducer, 1-D array, 1.5-D array, 1.75-D array, 2-D array, an annular array, or the like. Also the two CMUT structures 1011, 1012 may have the same or different configurations, i.e., one of CMUTs 1011, 1012 may be a single transducer, while the other may be an array of transducers, or other such combinations. Any of the foregoing exemplary implementations of stacked CMUTs may be used as component 1001, or other configurations that will be apparent based on the teachings disclosed herein. Further, while probe 1010 is described with reference to a HIFU procedure, other applications will also be apparent in light of the disclosure herein.

In some implementations, two stacked CMUT structures may be designed to operate in the same center frequency. However, in other implementations, for example, in HIFU applications, two CMUT structures may be configured to operate in different center frequencies. For example, one ultrasound transducer may be configured to operate at a lower center frequency (e.g. ~0.5-~3 MHz) for HIFU treatment and another ultrasound transducer may be configured to operate at a higher center frequency (e.g. ~5-~10 MHz) for imaging/treatment assessment. In using stacked CMUT structures to provide an ultrasound guided HIFU system, the second CMUT structure (e.g., CMUT 1012) may be configured to operate with a higher center frequency and may be constructed with a much more rigid structure than the first CMUT structure (e.g., CMUT 1011) that may be configured to operate with a lower center frequency. Therefore, when the transducer component 1001 operates at lower frequency for HIFU treatment, the second CMUT 1012 behaves like a surface plate or a flexible element of the first CMUT 1011 having a lower mass, more rigid hollow structure. Similarly, when the second CMUT 1012 in the transducer component 1001 operates at the higher frequency for imaging, there is almost no net electrostatic force applied on the first CMUT 1011 during the transmission period of the second CMUT. Furthermore, when an acoustic wave impinges on the transducer component 1001 during a reception period of the second CMUT 1012, the presence of the first CMUT structure 1011 has very little effect on the reception ability of the second CMUT 1012 because the frequency of the incoming acoustic wave is much higher than the frequency of operation of the first CMUT 1011. Therefore, acoustically, the two CMUT structures 1011, 1012 in the stacked transducer component 1001 are able to operate relatively independently.

Figure 11:
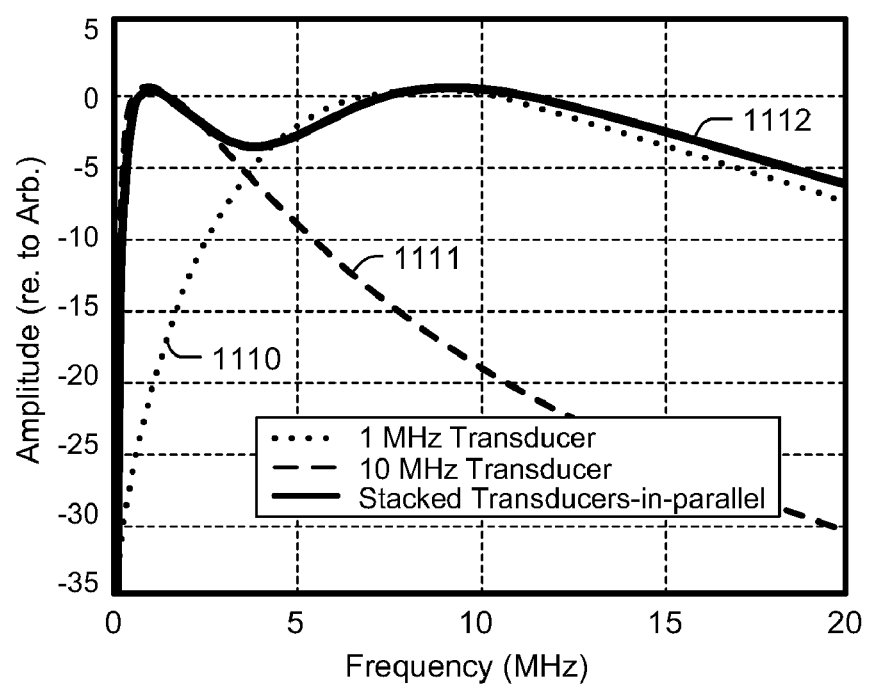
FIG. 11 illustrates exemplary graphic information of performance of stacked components according to implementations herein.

FIG. 11 illustrates an exemplary graphic simulation 1100 of a spectrum of an exemplary component having stacked CMUT. In this example, a component, such as those illustrated in any of FIGS. 1, 3-8 and 10 has two stacked CMUT structures that have center frequencies of 1 MHz and 10 MHz, respectively. For example, if two CMUT structures in the component are addressed separately (i.e., only one of the CMUTs is active), the graphic simulation 1100 illustrates the performance of a first one of the stacked CMUTs operating at 1 MHz, as indicated by a dotted line 1110, and the performance of a second one of the stacked CMUTs operating at 10 MHz, as indicated by a dashed line 1111. Further, when two CMUT structures are connected in parallel (i.e., both CMUTs are active), the transducer component illustrates an extremely wide bandwidth which covers both HIFU treatment and imaging frequency ranges so that the component can operate at both frequency ranges efficiently, as indicated by solid line 1112.

The stacked CMUT components are also useful in intravascular ultrasound applications (IVUS) and intracardiac echocardiography (ICE) due to the compact configuration of the components. In IVUS or ICE applications, the imaging is preferred to be at a lower frequency for larger volume imaging, but at a higher frequency for higher resolution imaging. One solution is to use two probes/transducers operating at different frequency ranges because a conventional transducer typically is not able to operate efficiently in both the lower and higher frequency ranges. However, switching between two transducers/probes dramatically increases the imaging time and also makes position registration between two different transducers/probes relatively difficult.

Implementations disclosed herein provide a single component or probe which can operate in two substantially different frequency ranges and/or have an extremely wide bandwidth able to cover an entire desired frequency range. The components disclosed herein having stacked CMUT structures are able to operate at two different frequency ranges, either as two independent transducers if each CMUT is independently addressed, or to operate as a single transducer to cover two different frequency ranges if the two CMUTs are connected in parallel. Position registration between two CMUT structures overlaid to form a single component is easy and accurate. Further, switching imaging capabilities between two frequency ranges (e.g., low resolution to high resolution) is easily accomplished because there is no need to physically exchange two separate probes. Also, when the two frequency ranges complement each other, the transducer has an extremely wide bandwidth which may cover the entire frequency ranges required for particular imaging procedures. Implementations of components disclosed herein having stacked CMUT structures are not much large than single conventional transducers, and are able to simply replace conventional transducers in various intravascular probes. The stacked CMUT structures in the components disclosed herein can be designed to be any configuration, e.g., a single element transducer, 1-D array, 1.5-D array, 1.75-D array, 2-D array, an annular array, etc. Also two stacked CMUT structures may have the same or different configurations, as discussed above.

Figure 12A:
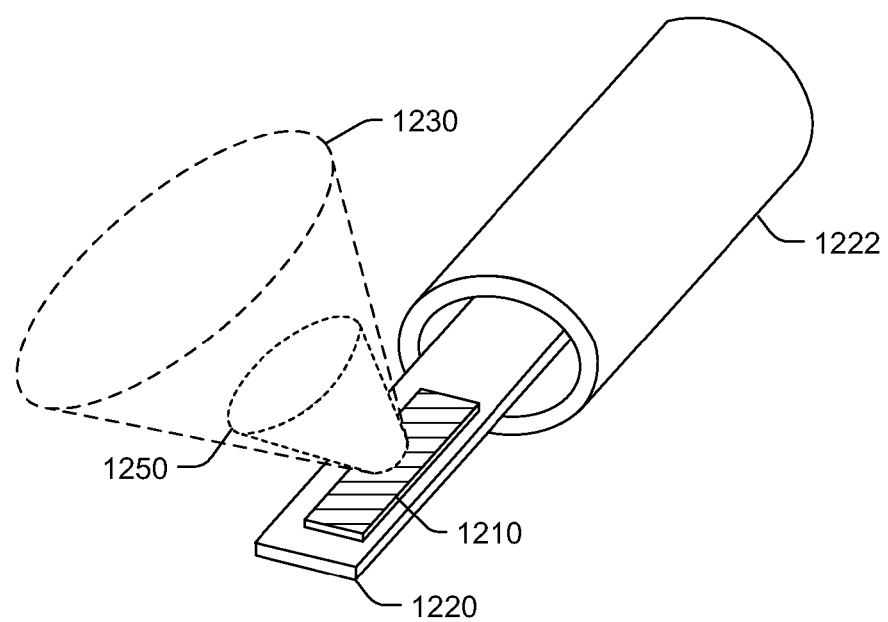
FIGS. 12A-12B illustrate an exemplary implementation of a system including a stacked component according to implementations herein.
Figure 12B:
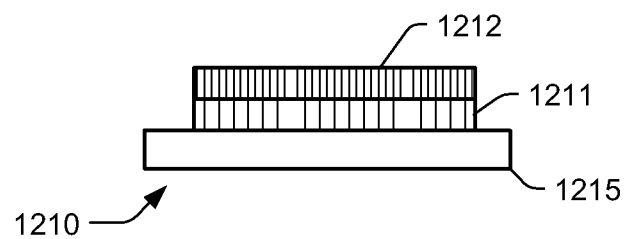

FIGS. 12A and 12B illustrate an exemplary implementation of a system 1200 including a component 1210 having stacked transducers used as a rotated transducer or transducer array in an IVUS or ICE probe catheter. A catheter 1222 includes a coaxially movable probe 1220 located in the annulus of the catheter. Probe 1220 may be extensible from the distal aperture of catheter 1222 and probe 1220 includes a component 1210 mounted thereon. As illustrated in FIG. 12B, component 1210 includes a first CMUT 1211 having a second CMUT 1212 located thereon according to implementations disclosed herein. First CMUT 1211 may optionally be formed on a substrate 1215. First CMUT 1211 may be configured to carry out ultrasonic imaging at a first frequency for achieving imaging at a first imaging field 1230, while second CMUT 1212 may be configured to carry out ultrasonic imaging at a second frequency for achieving imaging at a second imaging field 1250.

Figure 13A:
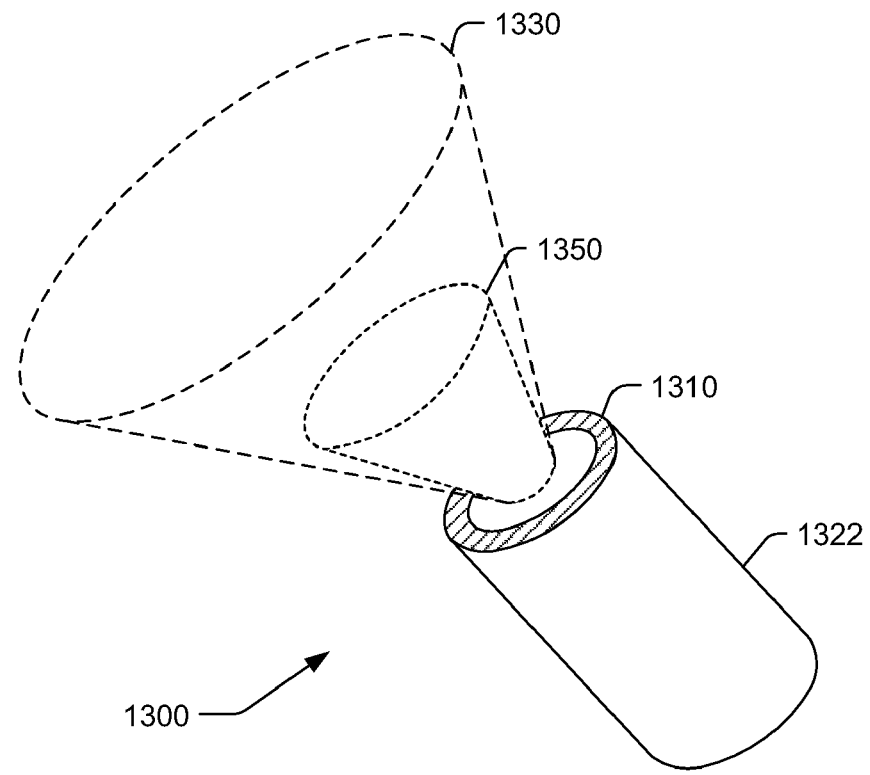
FIGS. 13A-13B illustrate an exemplary implementation of a system including a stacked component according to implementations herein.
Figure 13B:
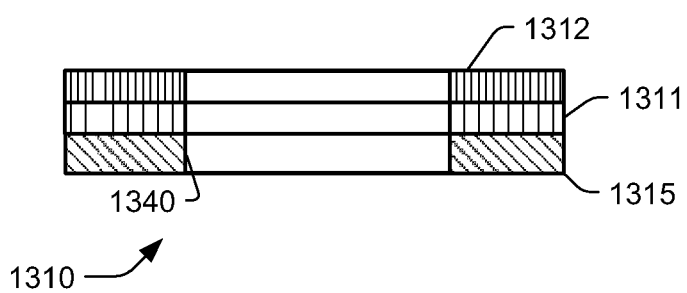

FIGS. 13A and 13B illustrate an exemplary implementation of a system 1300 for using a component having stacked transducers as a transducer or transducer array in a forward-looking probe or catheter 1322. Probe 1322 may be used for IVUS/ICE imaging or other imaging purposes. Probe 1322 includes an annular transducing component 1310 mounted on its distal end for carrying out ultrasonic imaging. As illustrated in FIG. 13B, component 1310 includes a first CMUT 1311 having a second CMUT 1312 located thereon according to implementations disclosed herein. First CMUT 1311 may optionally be formed on a substrate 1315, and first CMUT 1311 and second CMUT 1312 may each be an array of radially arranged CMUTs (e.g. a ring array) positioned about a central annulus 1340. First CMUT 1311 may be configured to carry out ultrasonic imaging at a first frequency for achieving imaging at a first imaging field 1330, while second CMUT 1312 may be configured to carry out ultrasonic imaging at a second frequency for achieving imaging at a second imaging field 1350.

Figure 14A:
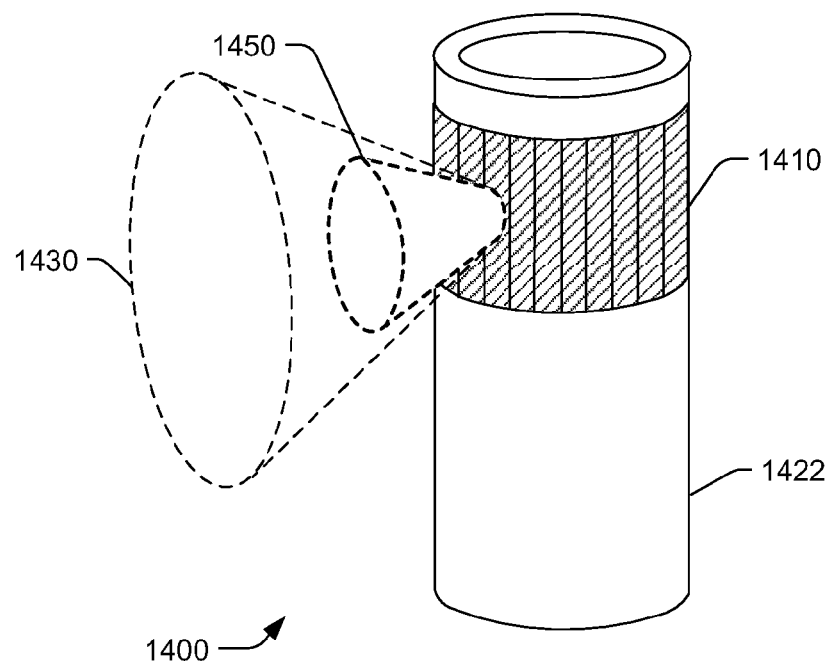
FIGS. 14A-14B illustrate an exemplary implementation of a system including a stacked component according to implementations herein.
Figure 14B:
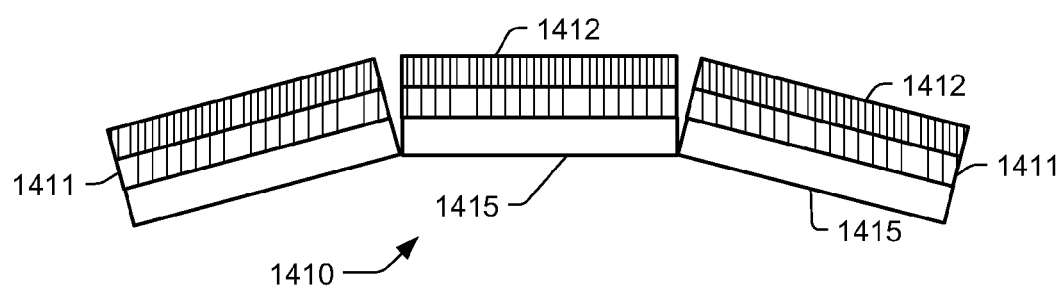

FIGS. 14A and 14B illustrate an example of a system 1400 including a component 1410 having stacked transducers as a transducer or transducer array in a sideway-looking probe or catheter 1422. Probe 1422 may be an IVUS/ICE probe catheter or other type of imaging probe or catheter. Probe 1422 includes an annular component 1410 mounted around the circumference of a distal end of probe 1422. As illustrated in FIG. 14B, component 1210 includes a plurality of first CMUTs 1411 having second CMUT 1412 located thereon according to implementations disclosed herein. First CMUTs 1411 may optionally be formed on a substrate 1415, and a plurality of the stacked CMUTs 1411, 1412 may be assembled around the outer circumference of probe 1422, thus forming a circumferential array of stacked CMUTs. First CMUTs 1411 may be configured to carry out ultrasonic imaging at a first frequency for achieving imaging at a first imaging field 1430, while second CMUT 1412 may be configured to carry out ultrasonic imaging at a second frequency for achieving imaging at a second imaging field 1450.

Moreover, the two CMUT structures 1211 and 1212, 1311 and 1312, and 1411 and 1412, in FIGS. 12-14, respectively, can be configured to operate for imaging and HIFU, as discussed above with respect to the implementations of FIGS. 10A-10B. Usually, both HIFU and imaging need to focus ultrasound into an imaging zone or ablation zone, the major differences are the frequency and the energy used in each operation. In this case, one of the CMUT structures operates at low frequency and is usually is configured to perform HIFU, while the other CMUT structure operates at high frequency and is usually configured to perform imaging. For example, in the implementations of FIGS. 12-14, one of the CMUT structures (e.g., 1211, 1311, 1411) on each respective probe is configured to operate at a frequency for carrying out HIFU, while the other CMUT structure (e.g., 1212, 1312, 1412) on each respective probe is configured to operate at a frequency for carrying out imaging. Other uses and applications for the implementations disclosed herein will also be apparent to those of skill in the art in view of the disclosure.

From the foregoing, it will be apparent that implementations disclosed herein provide components, systems and methods for implementing a plurality of CMUTs in a vertically stacked or overlaid configuration as a contiguous single component. Furthermore, some implementations are based on an ESCMUT, and a second CMUT can be stacked on a surface plate of the ESCMUT. In other implementations, the second structures built on the CMUT are other transducing devices such as interface circuits or sensors, e.g., pressure sensors, temperature sensors, flow sensors, or the like. Moreover, in some implementations, two CMUT structures can be built directly, one on the other, based on an ESCMUT design. Furthermore, in some implementations, the surface plate of one of the CMUTs can be patterned to a certain shape to improve CMUT performance, as well as to minimize the interference between the operation of two CMUT structures. In some implementations, the stacked CMUT structures may be used in different combinations to achieve desired functions and performance for selected applications, such as separate transmission and reception functions, double transmission, double reception, or independently operated CMUTs, as is discussed further below. The implementations set forth herein not only greatly improve CMUT design flexibility to adapt to an ultrasound system, but are also able to dramatically improve the transducer performance. In some implementations, the locations of two stacked transducer structures are defined by lithography, thus enabling the accurate registration of two transducers, one constructed on top of the other. The transducing devices and CMUT structures in the stacked configurations disclosed herein can be designed to be any configuration, e.g., a single element transducer, a 1-D array, 1.5-D array, 1.75-D array, 2-D array or annular array etc. Also two stacked CMUT structures may have the same or different configurations.

Implementations also relate to methods, systems and apparatuses for making and using the components described herein. Further, it should be noted that the configurations illustrated in FIGS. 1, 3-8, 10 and 12-14 are purely exemplary of components and systems in which the implementations may be provided, and the implementations are not limited to a particular hardware configuration. In the description, numerous details are set forth for purposes of explanation in order to provide a thorough understanding of the disclosure. However, it will be apparent to one skilled in the art that not all of these specific details are required.

Figure 15A:
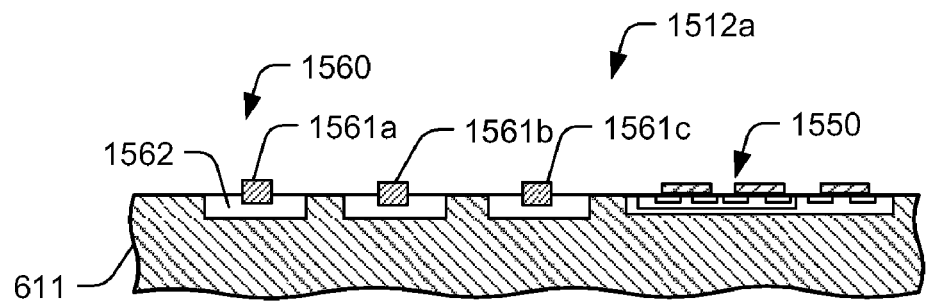
FIG. 15A illustrates a cross-sectional view of an exemplary implementation of a component including a CMUT and a flow/temperature sensor.
Figure 15B:
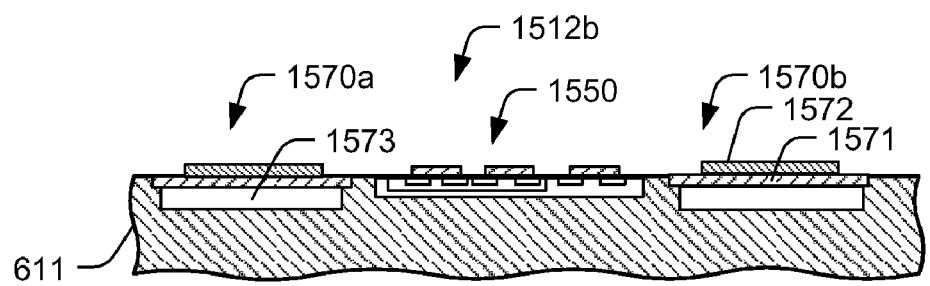
FIG. 15B illustrates a cross-sectional view of an exemplary implementation of a component including a CMUT and a flow/pressure sensor.

FIGS. 15A-15B illustrate additional exemplary implementations of components corresponding to FIG. 1 which have transducing devices 112 overlaid on CMUT structure 111. FIG. 15A illustrates a first exemplary transducing device 1512a built on a surface plate 611 of a CMUT structure 1511a, corresponding to the ESCMUT of FIG. 6. In other implementations, CMUT structure 1511a may be other known CMUT structures. For example, transducing device 1512a may be constructed on a flexible element/electrode 722/721 of a CMUT structure, such as that of second CMUT structure 712, as illustrated in FIG. 7. The exemplary transducing device 1512a may be a hot-wire flow sensor or a temperature sensor 1560. Optionally, one or more integrated circuits (ICs) 1550 may be integrated with sensor 1560. Sensor 1560 includes one or more wires 1561, with three wires 1561a-1561c being illustrated in the implementation of FIG. 15A. A cavity 1562 is located underneath each of the wires 1561a-1561c to reduce the thermal loading on the wires 1561 to improve the sensitivity of sensor 1560. If the sensor 1560 is configured as a flow sensor, then the middle wire 1561b is designed as a heater (i.e., a resistance-heated wire) which can be made of a conductive material and used to measure flow in a known manner. The wires 1561a and 1561c may be configured to be the temperature sensors and may be made of a material (e.g., platinum) having properties that change with temperature variation. The temperature difference between the wires 1561a and 1561c can be used to determine the flow information. Since the wire 1561a or the wires 1561c are sensitive to temperature change, sensor 1560 may also be used just as a temperature sensor. Furthermore, compared with conventional PZT transducers, the CMUT generates very little heat during operation, so the sensor of transducing device 1512a and CMUT 1511b are able to be operated independently.

FIG. 15B illustrates another exemplary implementation of a transducing device 1512b built on a surface plate 611 of a CMUT structure 1511b, corresponding to the ESCMUT of FIG. 6. In other implementations, CMUT structure 1511b may be other known CMUT structures. For example, transducing device 1512b may be constructed on a flexible element/electrode 722/721 of a CMUT structure, such as that of second CMUT structure 712, as illustrated in FIG. 7. In the illustrated implementation, transducing device 1512b includes two pressure sensors 1570a and 1570b that are built on the CMUT 1511b a desired distance apart. Optionally, an IC 1550 can be fabricated with the pressure sensors 1570a and 1570b. The pressure differential between two pressure sensors is able to provide flow information for a medium in the adjacent field. The pressure sensors 1570a and 1570b illustrated in FIG. 15B may be electrostatic pressure sensors, each comprising a flexible membrane 1571, a sealed cavity 1573, a top electrode 1572 and a bottom electrode, which is plate 611 in this implementation. Thus, the bottom electrode 611 may also be the top electrode 611 of the CMUT structure 1511B. Optionally, other pressure sensors, like piezoelectric pressure sensors, can be used in transducing device 1512b. Since the CMUT 1511b and pressure sensors (or flow sensor) of transducing device 1512b operate in respective frequencies having more than a two-order of magnitude difference, the pressure sensor (or flow sensor) 1512b and CMUT 1511b can be operated independently of each other.

In some applications, implementations such as those of FIGS. 15A and 15B provide additional functionality not currently available. For example, when ultrasound imaging is performed in vivo, blood flow information also may be desired during some procedures. By incorporating flow/pressure/temperature sensors into one or more CMUTs according to the implementations herein, these metrics can be monitored simultaneously with an imaging or treatment procedure. Further, while the transducing devices 1512 of FIGS. 15A-15B are discussed as being implemented on top of a single CMUT 1511, it should be noted that these transducing devices may be implemented on a component having a stacked CMUT structure as well. For example, transducing devices 1512a or 1512b may be implemented on top of second CMUT structure 712 of component 700 of FIG. 7, or on top of second CMUT structure 812 of FIGS. 8A-8B. Additionally, while some implementations are discussed above as components having two CMUT structures stacked one on top of the other, it is also within the scope of the disclosure and claims to have three or more CMUTs or other transducing devices as disclosed herein stacked one on top of the other, such as for operating at three different frequencies, or the like.

Although the subject matter has been described in language specific to structural features and/or methodological acts, it is to be understood that the subject matter defined in the appended claims is not limited to the specific features or acts described above. Rather, the specific features and acts described above are disclosed as example forms of implementing the claims. Additionally, those of ordinary skill in the art appreciate that any arrangement that is calculated to achieve the same purpose may be substituted for the specific implementations disclosed. This disclosure is intended to cover any and all adaptations or variations of the disclosed implementations, and it is to be understood that the terms used in the following claims should not be construed to limit this patent to the specific implementations disclosed in the specification. Rather, the scope of this patent is to be determined entirely by the following claims, along with the full range of equivalents to which such claims are entitled.

The invention claimed is:

1. A probe comprising:
   a first capacitive micromachined ultrasonic transducer (CMUT) mounted on the probe; and
   a second CMUT contiguous with the first CMUT in a stacked relationship, the second CMUT including a plate, wherein the plate is rigid relative to a first frequency of acoustic energy and flexible relative to a second frequency of acoustic energy.

2. The probe according to claim 1, wherein the first CMUT is configured to operate within the first frequency of acoustic energy and the second CMUT is configured to operate within the second frequency of acoustic energy.

3. The probe according to claim 1, wherein the first CMUT comprises:
   a first electrode;
   a second electrode separated from the first electrode by a first gap maintained by one or more first supports; and
   a spring member for enabling the first electrode and the second electrode to move toward and away from each other due, at least in part, to the first gap.

4. The probe according to claim 3, wherein:
   the second CMUT comprises the second electrode and a third electrode; and
   the third electrode is separated from the second electrode by a second gap on the opposite side of the second electrode from the first electrode, the second gap being maintained by one or more second supports.

5. The probe according to claim 4, wherein the third electrode is mounted on the plate such that flexing of the plate enables the third electrode to move toward and away from the second electrode due, at least in part, to the second gap.

6. The probe according to claim 3, wherein:
   the third electrode is formed as at least part of the plate, the plate overlying the second electrode and the spring member, and separated therefrom by a second gap maintained by one or more second supports;
   flexing of the plate allows the third electrode to move toward and away from the second electrode.

7. The probe according to claim 3, wherein:
   the second CMUT comprises the second electrode and a third electrode;
   the third electrode is separated from the second electrode by a second gap on the opposite side of the second electrode from the first electrode, the second gap being maintained by one or more second supports; and
   the third electrode is located primarily over one or more of the first supports such that operation of the second CMUT has minimal effect on operation of the first CMUT.

8. The probe according to claim 1, wherein the first CMUT and the second CMUT share a common middle electrode.

9. The probe according to claim 1, wherein:
the first CMUT is connected to a reception circuit to receive acoustic energy; and
the second CMUT is connected to a transmission circuit to transmit acoustic energy.

10. The probe according to claim 1, wherein the first CMUT and the second CMUT are connected to a circuit for selectively connecting the first CMUT and second CMUT to:
a transmission circuit for enabling the first CMUT and second CMUT to transmit acoustic energy; or
a reception circuit for enabling the first CMUT and the second CMUT to receive acoustic energy.

11. The probe according to claim 1 wherein:
the first CMUT and the second CMUT are connected in parallel;
first CMUT is connected to a first circuit for selectively connecting the first CMUT to one of a first transmission circuit or a first reception circuit; and
the second CMUT is connected to a second circuit for selectively connecting the second CMUT to one of a second transmission circuit or a second reception circuit.

12. The probe according to claim 1, wherein:
the first CMUT is configured as an imaging transducer for providing a field of view of tissue during a surgical procedure; and
the second CMUT is configured to focus ultrasonic energy on a desired area of tissue for carrying out tissue ablation during the surgical procedure.

13. The probe according to claim 1, wherein:
the first CMUT is configured as an imaging transducer for providing imaging at a first operation frequency range that includes the first frequency of acoustic energy; and
the second CMUT is configured as an imaging transducer for providing imaging at a second operation frequency range, different from the first operation frequency range, the second operation frequency range including the second frequency of acoustic energy.

14. The probe according to claim 1, further comprising at least one of a flow sensor or a temperature sensor located on the plate of the second CMUT.

15. The probe according to claim 1, further comprising a pressure sensor located on the plate of the second CMUT.

16. A probe comprising:
a first electrode;
a second electrode separated from the first electrode by a first gap;
a spring member and one or more first supports for maintaining the first gap between the first electrode and the second electrode, wherein the first electrode and the second electrode are able to move toward or away from each other at least in part by flexing of the spring member; and
a third electrode separated from the second electrode by a second gap on an opposite side of the second electrode from the first electrode, wherein:
a first capacitive micromachined ultrasonic transducer (CMUT) comprises the first and second electrode;
a second CMUT comprises the second electrode and the third electrode; and
the first CMUT and the second CMUT are addressed separately such that the first CMUT is configured for a first operation frequency for achieving imaging in a first imaging field and the second CMUT is configured for a second operation frequency for achieving imaging in a second imaging field, different from the first imaging field.

17. The probe according to claim 16, wherein:
the second electrode is a first plate;
the third electrode is contiguous with a second plate that is separated from the first plate by one or more second supports; and
the second plate is rigid relative to the first operation frequency and flexible relative to the second operation frequency.

18. The probe according to claim 16, wherein:
the second electrode is contiguous with the spring member;
the third electrode is associated with a plate separated from the second electrode and the spring member by one or more second supports; and
the plate is rigid relative to the first operation frequency and flexible relative to the second operation frequency.

19. The probe according to claim 18, wherein the third electrode is located over one or more of the first supports such that movement of the third electrode toward and away from the second electrode has minimal effect on relative movement between the first and second electrodes.

20. The probe according to claim 16,
wherein the first electrode and the second electrode comprise a first capacitive micromachined ultrasonic transducer (CMUT);
wherein the second electrode and the third electrode comprise a second CMUT; and
wherein the second electrode is connected to a bias or voltage source and serves as a common electrode to the first and second CMUTs.

21. A probe comprising:
a first transducer mounted on the probe; and
a second transducer contiguous with the first transducer in a stacked relationship, wherein the first transducer and the second transducer are addressed separately such that the first transducer is configured for a first operation frequency for achieving imaging in a first field of view and the second transducer is configured for a second operation frequency for achieving imaging in a second field of view, different from the first field of view.

22. The probe according to claim 21, wherein:
the first transducer is a first capacitive micromachined ultrasonic transducer (CMUT) and
the second transducer is a second CMUT including a plate that is rigid relative to the first operation frequency and flexible relative to the second operation frequency.

23. The probe according to claim 21, wherein the first operation frequency is for low resolution imaging and the second operation frequency is for high resolution imaging.

* * * * *